United States Patent
Graves et al.

Patent Number: 5,342,498
Date of Patent: Aug. 30, 1994

[54] ELECTRONIC WIRING SUBSTRATE

[76] Inventors: Jeffrey A. Graves, 31832 Via Flores, San Juan Capistrano, Calif. 92675; Marshall L. Sherman, 875 Nolbey St., Cardiff, Calif. 92007; Matthew J. Leader, 48 Oakcliff Dr., Laguna Niguel, Calif. 92677; Kee V. Sin, 7181 Sunfish Ct., Lino Lakes, Minn. 55014

[21] Appl. No.: 905,254

[22] Filed: Jun. 26, 1992
(Under 37 CFR 1.47)

Related U.S. Application Data

[63] Continuation-in-part of Ser. No. 721,030, Jun. 26, 1991, abandoned.

[51] Int. Cl.⁵ ............................................. G01N 27/26
[52] U.S. Cl. ................................... 204/408; 204/406; 204/403; 204/412; 204/433; 204/435
[58] Field of Search ............... 204/409, 406, 408, 412, 204/416, 422, 433, 435, 403; 338/22 R; 128/635; 219/209, 121.6

[56] References Cited

U.S. PATENT DOCUMENTS

| | | | |
|---|---|---|---|
| 3,000,805 | 9/1961 | Carritt | 204/195 |
| 3,049,118 | 8/1962 | Arthur et al. | 128/2 |
| 3,395,265 | 7/1968 | Weir | 219/209 |
| 3,440,397 | 4/1969 | Vesper et al. | 219/209 |
| 3,440,407 | 4/1969 | Goltsos et al. | 219/494 |
| 3,497,442 | 2/1970 | Vincent | 204/195 |
| 3,887,785 | 6/1975 | Ahlport | 219/209 |
| 4,041,440 | 8/1977 | Davis et al. | 338/195 |
| 4,133,735 | 1/1979 | Afromowitz et al. | 204/195 G |
| 4,284,872 | 8/1981 | Graeme | 219/121 LJ |
| 4,312,332 | 1/1982 | Zick | 128/635 |
| 4,356,379 | 10/1982 | Graeme | 219/209 |
| 4,450,842 | 5/1984 | Zick et al. | 128/635 |
| 4,454,007 | 6/1984 | Pace | 204/1 T |
| 4,481,403 | 11/1984 | Del Monte | 219/209 |
| 4,536,274 | 8/1985 | Papadakis et al. | 204/433 |
| 4,734,184 | 3/1988 | Burleigh et al. | 204/409 |
| 4,818,361 | 4/1989 | Burgess et al. | 204/406 |
| 4,855,572 | 8/1989 | Wallgren et al. | 219/456 |
| 4,863,016 | 9/1989 | Fong et al. | 206/210 |
| 4,929,426 | 5/1990 | Bodai et al. | 422/63 |
| 5,017,340 | 5/1991 | Pribat et al. | 204/424 |
| 5,043,692 | 8/1991 | Sites et al. | 338/22 R |
| 5,046,496 | 9/1991 | Betts et al. | 128/635 |
| 5,096,669 | 3/1992 | Lauks et al. | 422/61 |

OTHER PUBLICATIONS

U.S. Ser. No. 07/905,255, filed Jun. 26, 1992 entitled "Integrated Circuit Hydrated Sensor Apparatus".
U.S. Ser. No. 07/721,028, filed Jun. 26, 1991 entitled "Fluid Sample Analyte Collector and Calibration Assembly".
U.S. Ser. No. 07/721,025, filed Jun. 26, 1991 entitled "Integrated Circuit Hydrated Sensor Apparatus".
U.S. Ser. No. 07/721,027, filed Jun. 26, 1991 entitled "Electrochemical Sensor Storage Device".

*Primary Examiner*—John Niebling
*Assistant Examiner*—Bruce F. Bell

[57] ABSTRACT

An improved electronic wiring board having a thermistor and at least one blood gas sensor supported, in close relation, one to the other, on one side of the board and a heater supported on the other side of the board to provide heat in response to temperature sensed by the thermistor, to at least the region where the thermistor and the blood gas sensor are positioned on the board to control the temperature of the region of the board within a narrow distribution of temperatures.

31 Claims, 4 Drawing Sheets

ELECTRONIC WIRING SUBSTRATE

This application is a continuation-in-part application of Ser. No. 07/721,030 filed Jun. 26, 1991, now abandoned.

FIELD OF THE INVENTION

The present invention is related to an improved electronic wiring substrate like a wiring board useful for detecting one or more analytes and their amounts in fluid samples.

BACKGROUND OF THE INVENTION

Numerous methods and apparatus exist in the art for measuring chemical components of fluids, and current technology utilizes many types of sensors for detecting components, analytes, in numerous types of fluids. For example, some of these range from oxygen sensors for detecting oxygen in air for control of the air and fuel ratio for combustion in internal combustion engines to multiple phase sequential analyzers for qualitative and/or quantitative measurement of constituents or analytes of blood. For instance, the measurement of blood gases, usually a measure of the partial pressures of oxygen and carbon dioxide, along with the pH from a sample of arterial blood gives the state of the acid base balance or the effectiveness of both the respiratory and cardiovascular systems of the human or vertebrate body. These various types of sensors can be prepared by various techniques including layered circuit or integrated circuit technologies, as for example, thick film, thin film, plating, pressurized laminating and photolithographic etching, and other like silk screening processes.

In many of the existing measurement methods, when the fluid is a liquid or liquid with a dissolved gas with or without the presence of solids, it may be necessary to transport a sample to a central location for testing. With centralized testing, the bulky, stationary, elaborate and sophisticated equipment performs the analysis on a practically endless number of samples. An example of this is the qualitative and/or quantitative measurement of constituents or analytes of blood. For instance, the measurement of blood gases, usually a measure of the partial pressures of oxygen and carbon dioxide, along with the pH from a sample of arterial blood gives the state of the acid base balance or the effectiveness of both the respiratory and cardiovascular systems of the human or vertebrate body. For measuring constituents of blood, the blood sample is drawn from the patient and usually, as in the case of blood gases, transported to a central location for testing.

This technique of transporting the sample to stationary measuring equipment can lead to problems. Ingenious technology has broached solutions to maintain the original composition of the fluid during transportation. Elaborate designs for syringes used in taking the blood samples overcame some problems that resulted in inaccurate readings of the particular chemical constituent being measured. For instance, in determining blood gas composition, the problem of air contamination in the collected sample was solved by the use of liquid heparin as an anticoagulant. Unfortunately, this introduced a sample dilution problem. Subsequent development resulted in the use of heparin in the dry state as opposed to the liquid state to avoid this dilution. Also, elaborate designs provided for proper mixing of the sample after transportation but before testing. Even with these improvements, there are many reports in the literature that suggest that the values obtained in the measurement of blood gases depend on the type of measuring equipment and the technique for sample collection.

The art also has attempted to develop more portable measuring equipment rather than the fairly expensive nonportable equipment that engender the elaborate and cumbersome transportation techniques. Devices that are very portable could shorten or overcome transporting the sample altogether so that a patient's blood gases could be measured at the bedside in a manner similar to measuring a patient's temperature. U.S. Pat. Nos. 3,000,805 and 3,497,442 show two such devices. The former has electrodes located on a syringe plunger and the latter has electrodes placed on the syringe well to conduct the measurements. The electrodes are the sensing devices for the blood gases. In the allowed U.S. patent application Ser. No. 07/343,234, now U.S. Pat. No. 5,046,496. Applicants assignee describes and claims a portable blood gas sensor which includes electrodes fabricated from a conventional silk screening process where the electrodes are screened on to a ceramic substance. Typically these electrodes are used along with an electrolyte and analyte permeable membrane that covers the sensor. Some of these membranes may be hydratable membranes that can be stored in a dry state and hydrated just prior to use.

The utilization of portable equipment to obtain accurate analysis reports while using a disposable device could be advanced with improvements in electronic circuit board design.

Accurate sensing of the ambient temperature of the wiring board is required to precisely control the heater to ultimately maintain, within a narrow distribution of temperatures, the desired operating surface temperature on the wiring board in the region the several sensors. Also the accurate sensing of temperature is important is the area of measuring two phase calibrant liquids so that the calibrant values can be corrected for the most recent storage temperature.

Placement of the all of the components, including the heater, on the wiring board is also very important to obtain the maximum utility and capability of these components and minimize power consumption.

SUMMARY OF THE INVENTION

The improved electronic wiring board of the present invention has a nonconducting substrate, a thermistor and at least one analyte sensor supported, in close relation, on the substrate, and a heater, also supported on the substrate, to provide heat in response to temperature sensed by the thermistor to at least the region where the thermistor and the blood gas sensor are positioned on the board to thereby control the temperature of the region of the board within a narrow distribution of temperatures and thereby increase the sensor's accuracy, and connecting means supported on the board for connecting the board to an external electrical source.

In a narrower aspect of the present invention the improved electronic wiring substrate is manufactured using thick film or thin film layered circuit technique or a combination of these, and the thermistor and the one or more analyte sensors are supported in the same plane on the substrate wherein the analyte sensors are blood gas sensors of one or more of the following types: an oxygen sensor, a carbon dioxide sensor, and a pH sensor. Also the connecting means includes plurality of external leads, and a resistor is supported on the substrate on the same side as the heater and commonly connected to one of the external leads with the thermistor, dividing the voltage therebetween. Although it is possible to have the resistor and the heater each electrically connected to external leads, the temperature coefficient of the thermistor can be positive or negative and the temperature coefficient of the resistor is substantially zero. Also the thermistor and resistor values are allowed to vary over several orders of magnitude as long as the two can be made equal at the calibration temperature. Additionally, the connecting means further includes a plurality of electronic conducting pathways individually and electrically connecting each of the sensors and the thermistor with external leads provided on the substrate at the end of the pathways. Also the heater is powered by a controlled DC voltage whereby the heater is regulated by a combination of proportional, integral and/or derivative controls thereby reducing the amount of overshooting or undershooting by the heater of a predetermined temperature. The external leads are positioned on the same side of the substrate as the resistor and the heater.

Another aspect of this invention is to provide an improved electronic wiring substrate wherein the electronic conducting pathways individually and electrically connecting each of the sensors and the thermistor on one side of the board with external leads provided on the other side of the board through a plurality of holes in the board.

Another aspect of this invention is to provide an improved electronic wiring substrate wherein the temperature sensor including the thermistor and the resistor is calibrated by laser trimming of the resistor to produce a ratiometric output proportional or inversely proportional to temperature.

A further aspect of this invention is to provide an improved electronic wiring substrate wherein the oxygen sensor is an electrochemical cell and includes a anode and a cathode, each connected to an external lead. Also the oxygen sensor includes an oxygen permeable membrane covering, in a fluid tight manner, and an opening in the board contains an electrolyte, and the anode is grounded on the board to thereby assure that the potential of the electrolyte is the same as the anode potential.

Another aspect of this invention is to provide an improved electronic wiring substrate wherein there is at least one reference electrode, to provide an accurate reference potential, supported on the board and is electrically connected to a electronic conducting pathway. Although it is possible to have one reference electrode present on the substrate and it is supported on the substrate and it is electrically connected to a electronic conducting pathway extending from the anode. The nonconducting substrate is a flat substantially thin ceramic substrate layer that has a patterned metallic layer provided on the ceramic substrate layer. The metallic layer can be formed on the substrate by depositing a metallic printing paste on the substrate to form electronic conducting pathways and the electrodes of the sensors and the electrode of a reference electrode. The metallic layer can be encapsulated with at least one layer of a chemically stable and moisture resistant encapsulant that provides electrical isolation of the electronic conducting pathways from the electrolyte to sample like blood. The wiring substrate as described can operate even after several months of storage. The thermistor provided on the ceramic substrate layer, can be encapsulated with at least one substantially thin layer of a chemically stable and moisture resistant encapsulant.

DETAILED DESCRIPTION OF THE INVENTION

Similar numerals are used throughout all of the drawings to denote similar features.

Figure 1:
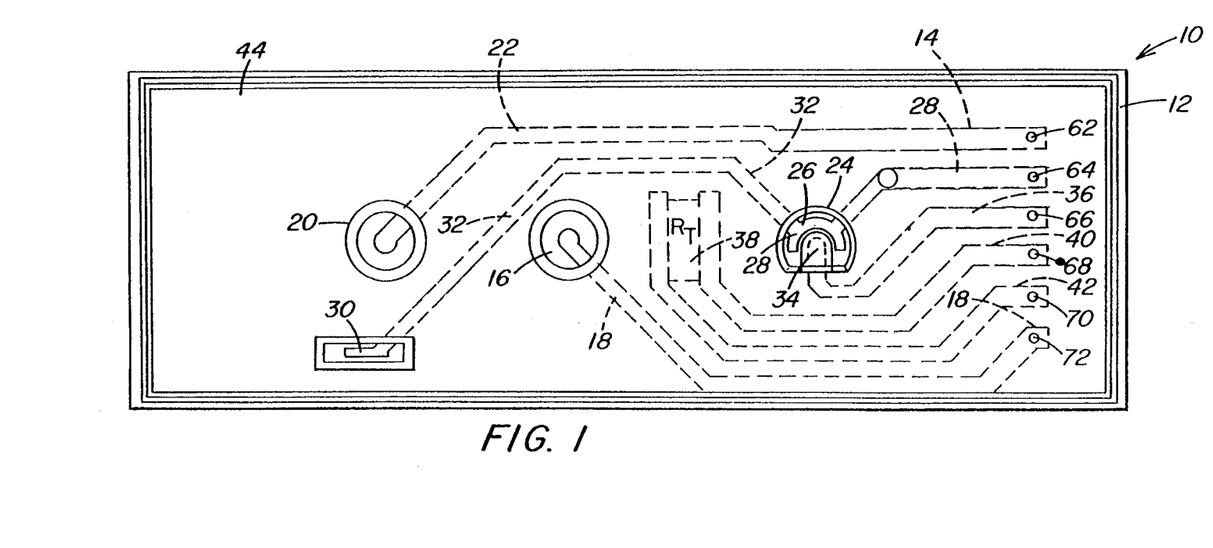
FIG. 1 is a top planar view of one side of the wiring substrate of the present invention, having electrodes and a thermistor.

FIG. 1 is a top planar view of one side of the wiring substrate, hereinafter referred to as "board" with at least one electrochemical sensor 10 of the present invention, where the components have particular shapes. Any other shapes than those shown in FIG. 1, that are known to those skilled in the art for the particular components, can be used.

The improved wiring board 10 may be produced from any number of well known layered circuit technologies, as for example, thick film, thin film, plating, pressurized laminating and photolithographic etching, however, the thick film technique is preferred.

Figure 2:
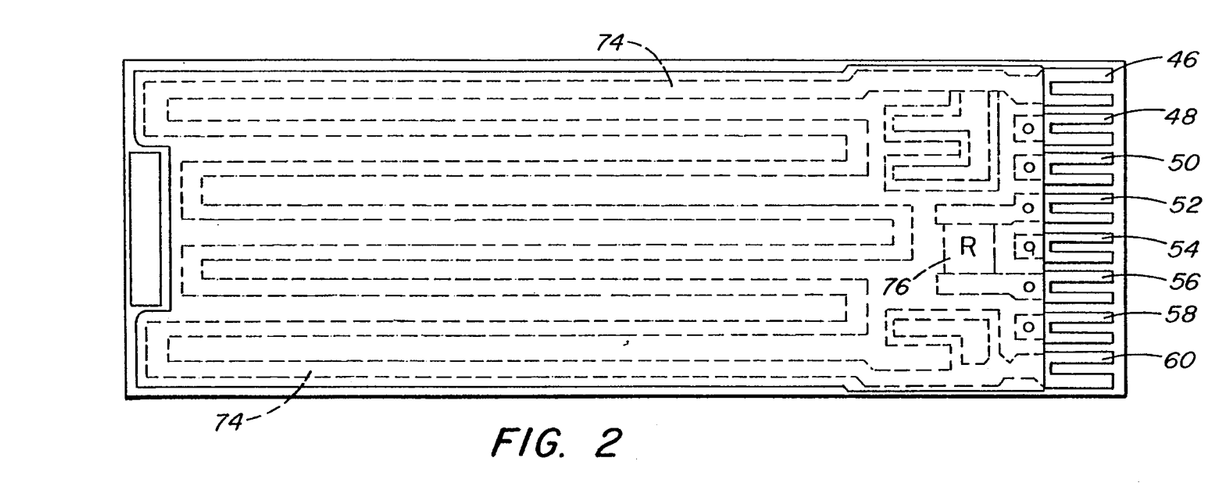
FIG. 2 is a planar view of the other side of the wiring substrate of FIG. 1 having a resistor and a heater that traverses the board and a number of leads through the substrate from the side depicted in FIG. 1 to provide an external electrical connection from the substrate.

The substrate 12 on both sides of the board 10 is any glass or ceramic including sheet or chip or nonconducting substrate like wood or nonconducting polymers or commercially available frit that can be used as the substantially smooth flat surface of the substrate layer 12. Nonexclusive examples include borosilicate glass as is known to those skilled in the art for producing thick film or layered circuits. A nonexclusive but preferred example of which includes a ceramic base having around 96% Al2O3 such as that available commercially from Coors Ceramic Company, Grand Junction, Colo.

The substrate layer 12 is essentially flat and any substrate known to those skilled in the art for forming printed wiring circuits can be used. It is preferred that the composition of the substrate can endure the presence of electrolyte that has a pH in or over the range of 6 to 9 and remain unaffected for a substantial period of time.

As can best be seen in FIG. 1, the board 10 is provided with a number of electrodes and more particularly, electrodes useful in the measurement of blood gas oxygen, carbon dioxide and pH. The board 10 is also provided with a thermistor and resistor arrangement to indicate the temperature at any time on the board 10 as well as reference electrodes for establishing an accurate reference potential; all of which will be described in further detail below.

Figure 5:
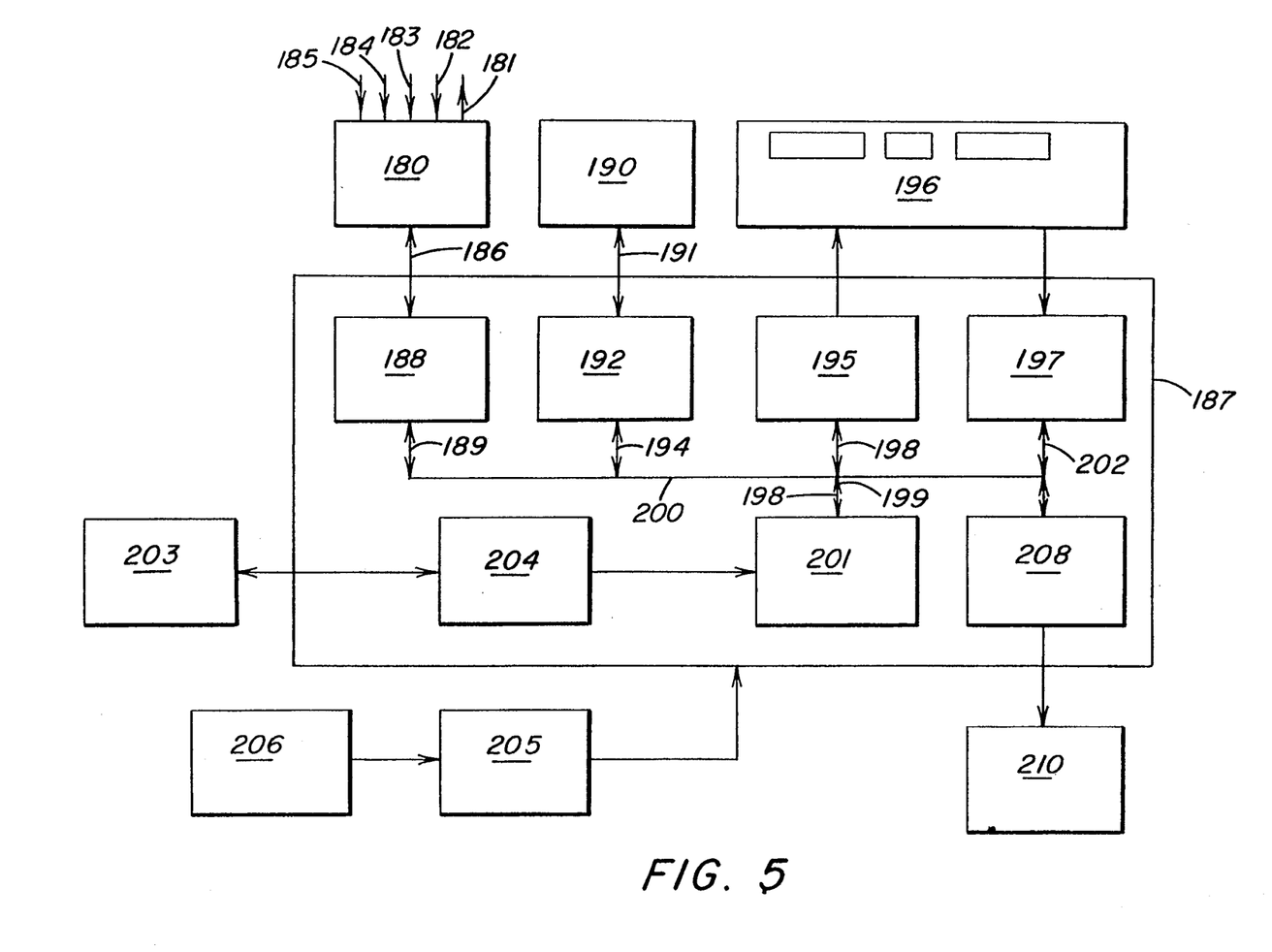
FIG. 5 is a block diagram of the monitoring means and its connection with the electronic wiring substrate.
Figure 6:
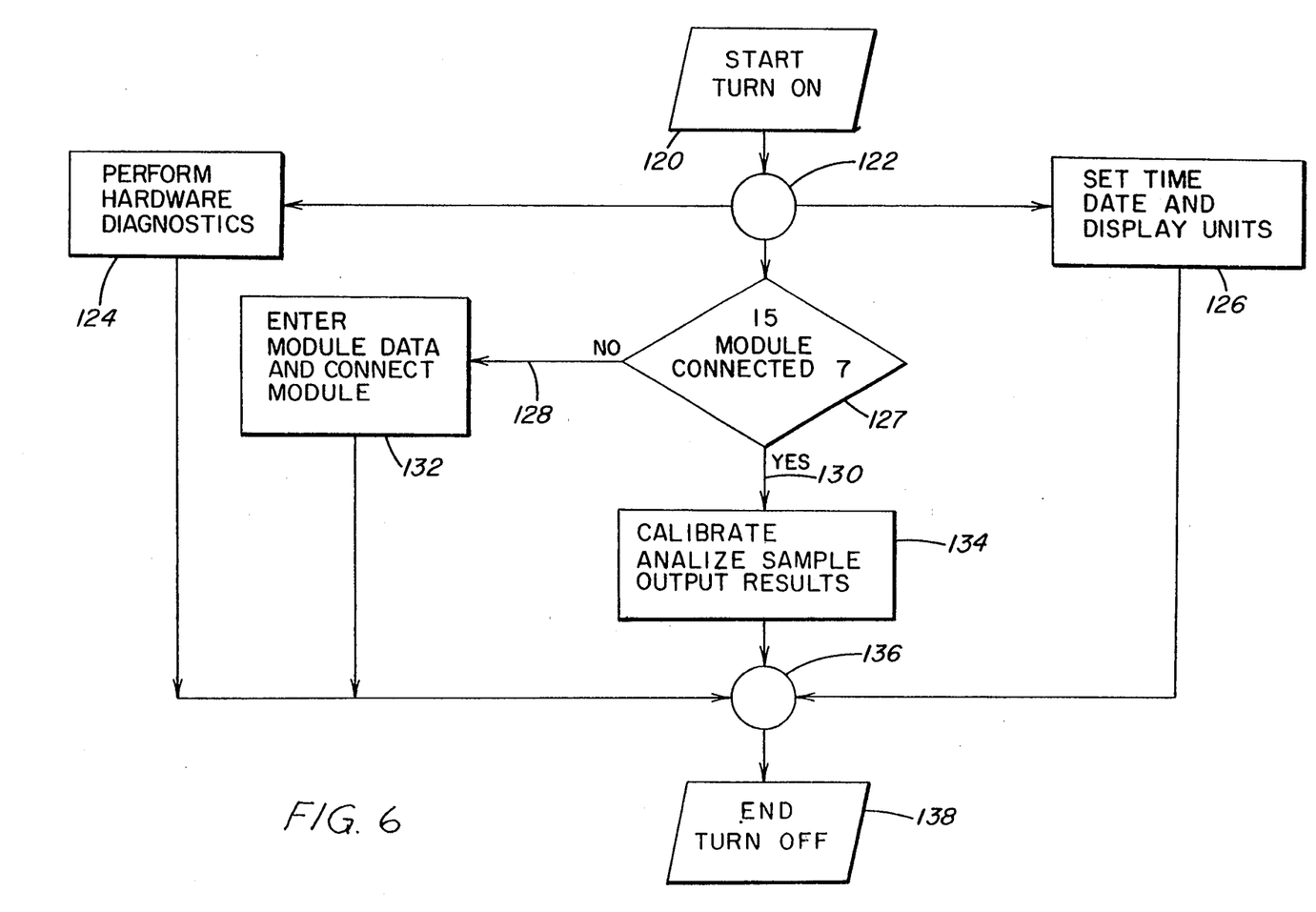
FIG. 6 is a block diagram of the flow chart of the software for the analyzer.

On the substrate layer 12 is a patterned metallic layer 14 with a number of extensions which act as the electronic conducting pathway between a voltage or current source external to the board 10 (not shown) and each of the components. The extensions constitute the transmission section, where each extension has a component at its end. The several extensions also have the ability to transmit changes in voltage from the components of the board 10 to an electronic analyzing module as shown in FIGS. 5 and 6.

The pH sensing electrode 16 is located at the end of extension 18; the carbon dioxide sensing electrode 20 is located at the end of extension 22; the oxygen sensor 24 is provided with an anode 26 located at the end of extension 28; the reference electrode 30 is located at the end of extension 32 which extends from anode 26 of the oxygen sensor 24; the oxygen sensor 24 is further provided with a cathode 34 which is located at the end of extension 36; thermistor 38 is located at the end of extensions 40 and 42.

As shown in FIG. 2, the patterned metallic layer 14 has metallic external leads 46–60 on the other side of the substrate 12. Although the external leads are shown on the opposite side of the substrate 12, they can also be on the same surface as their associated metallic lead patterns and components.

External leads 48–58 are conductively associated with the components on the FIG. 1 side of the substrate layer 12 and external leads 46 and 60 are in metallic electrical conducting contact with a thick film heater 74 which is provided on the FIG. 2 side of the substrate layer 12. The heater 74 traverses the board in a serpentine fashion to provide a grid of heat to the nonelectrically conducting substrate and its function will be described below.

External leads 52 and 56 are in metallic electrical conducting contact with a resistor 76 which is also provided on the FIG. 2 side of the substrate layer 12. The resistor is in a half-bridge relationship with the thermistor 38 and, as such, it commonly shares external lead 52 with the thermistor 38; thermistor 38 also being in metallic electrical conducting contact with external lead 52. The function of the thermistor 38 and resistor 76 arrangement will be described below.

The patterned metallic layer 14 is formed by printing pastes deposited onto a substrate in the desired pattern to act as ohmic conductors. Nonexclusive examples of suitable heat resisting metals include; noble metals such as platinum (Pt), ruthenium (Ru), palladium (Pd), rhodium (Rh), iridium (Ir), gold (Au) or silver (Ag) or other metals traditionally used as Clark cells and other ISE's and mixtures thereof. A nonexclusive but preferred example of a suitable paste is a silver paste of the type produced and available from Electro-Science Laboratories, Inc. under the trade designation ESL 9912.

The metallic layer 14 is dried to produce the above noted patterned conductive pathways 18, 22, 28, 32, 36, 38 and 40 of FIG. 1. Any method known to those skilled in the art for producing a sufficient thickness of metallic tracing can be used. Preferably pathway 28 has ground 29.

Preferably, the silver pastes are oven dried and fired at a high temperature in a furnace. Firing can be accomplished at a temperature in the range of around 800° C. to 950° C. for a period of around 1 to 20 minutes. With this procedure, the thickness of the layer of the metallic conducting tracing is usually in the range of around 0.0005 to 0.001 inches. Although the aforementioned are preferred conditions, general conditions for obtaining a proper thickness can be used where the thickness can be generally range from about 0.0004 to 0.0015 inches.

The aforementioned conductive patterns are encapsulated with a glass ceramic mixture or a ceramic insulating material such as alumina or spinal. This encapsulation can range from a total encapsulation to encapsulation except at the end of the metallic pattern.

The aforementioned electrodes are preferably produced by one of the layered circuit techniques. This involves leaving the respective shaped ends uncovered while the metallic patterns are completely covered by the encapsulant. The encapsulation of the metallic patterns can range from encapsulating each from the other to a sufficient degree for electrical insulation of the conductive patterns and any conductive layers from each other.

As shown in FIG. 1, the encapsulant can extend across the whole board from edge to edge as generally shown at numeral 44. Preferably, the thickness of the encapsulant layer is that which is adequate to seal the underlining metallic layer and to provide insulation for the metallic patterns. Preferably, the thickness of the layer is around 20–30 microns.

A preferred glass ceramic mixture useful as the encapsulant is the type produced and available from Electro-Science Laboratories, Inc. under the trade designation ESL 4904.

The several electrodes may be masked during the encapsulation to keep them suitably uncovered for the addition of active materials (e.g. polymer liquids and pre-cut dry film membranes) over the appropriate electrodes on the surface of the substrate layer 12.

This process involves masking the electrodes by the use of polymer film coating on the screen used to screen print the encapsulant. This leaves the underlying silver exposed to form the electrodes for active materials. It is also possible to use multiple layers of the metallic conductive layer or encapsulant.

Preferably, the glass composition for the encapsulant as with the substrate 12 is selected to possess good chemical stability and/or moisture resistance and to possess high electrical insulation resistance. Also, the metallic and encapsulant materials are selected so that they can endure the presence of an electrolyte in a similar manner as the substrate composition.

The geometry of the several electrodes could be made by a laser beam to carve or cut or trim the electrode, however, they are preferably prepared by the aforementioned layered circuit technique.

The serpentine formed heater 74 and the resistor 76 on the FIG. 2 side of the board may be prepared by a number of commercially available techniques, however, they are preferably thick film devices prepared by the aforementioned layered circuit technique.

Holes 62–72 may be drilled by a laser through the substrate 12 to conductively connect the metallic extensions 18, 22, 28, 38, 40 and 36 traced on the FIG. 1 side of the substrate layer 12 with their respective metallic external leads 48–58 on the FIG. 2 side of the substrate layer 12. In general, these openings 62–72 are produced by the focused laser beam drilling a hole by heating a small volume of material to a sufficiently high temperature for localized melting and/or vaporization.

The external leads 46–60 may be produced on the other side of the side of the substrate layer 12 with the same paste and firing as that done for aforementioned metallic patterns. The metallic external leads 46–60 are in metallic electrical conducting contact with the various components on each side of the board. As before mentioned external leads 46 and 60 are in metallic electrical conducting contact with the heater 74 and external leads 52 and 56 are in metallic electrical conducting contact with a resistor 76 which commonly shares external lead 50 with the thermistor 38; thermistor 38 also being in metallic electrical conducting contact with external lead 50. External lead 58 is in metallic electrical conducting contact with the $CO_2$ sensing electrode 20; external lead 48 is in metallic electrical conducting contact with the pH sensing electrode 16; external lead 48 is in metallic electrical conducting contact with the $CO_2$ sensing electrode 20; external lead 52 is in metallic electrical conducting contact with the anode 26 of the oxygen sensor 24, the anode 26 having an electrical ground 27; external lead 52 is also in metallic electrical conducting contact with the reference electrode 30 which is located at the end of extension 32 which extends from anode 26 of the oxygen sensor 24, the anode 26 and external lead 54 is in metallic electrical conducting contact with the cathode 34 of the oxygen sensor 24; external lead 54 is in metallic electrical conducting contact with the cathode 34 of the oxygen sensor 24.

The holes 62–72 have been drilled through the substrate layer 12 and when the metallic layers are screened such electrical connections are formed. Alternatively, the metallic external leads 46–60 can be produced and preferably are produced by a very high powered carbon dioxide laser. This can be accomplished by the supplier of the nonconducting substrate and in this case the metallic layer is added to the substrate so each conducting pathway electrically connects with an external lead.

As described above, the process of masking the electrodes by the use of polymer film coating on the screen, is used to screen print the encapsulant. This leaves the underlying silver exposed to form the electrodes for active materials. It is also possible to use multiple layers of the metallic conductive layer or encapsulant and the outer layer of the encapsulant may be solvent or thermoplastically bondable and may include polymers, as for example, acrylates or polyvinyl chloride as the major component in the encapsulant. The purpose of the outer coating or encapsulant is to enhance bonding of the active materials and, in particular, to provide a reliable surface for the attachment of the liquid or solid film type membrane materials.

Each of the sensing electrodes are fabricated to perform their specific task and may be selected from many commercially available electrode components. The pH electrode 16, $CO_2$ electrode 24 and the Oxygen sensor 24 are each fabricated with a membrane which maintains their respective electrolytes in a fluid tight manner in the cavities or openings in which the electrodes are positioned.

The pH electrode 16 and the $CO_2$ electrode 20 may be similar in regards to the circuit geometry and electrolyte and may be provided with membranes suitable for the particular characteristic being measured.

For pH electrode 16, for example, the use of cation permeable and particularly hydrogen ion permeable membrane may be used. A number of such cationic exchange materials may be utilized, as for example, membranes fabricated from copolymeric vinyl ethers as manufactured by E. I. duPont under registered trademark NAFION.

The membrane for the $CO_2$ electrode 20 may be fabricated from a wide range of commercially available carbon dioxide permeable polymeric materials. The electrolytes of the pH electrode 16 and the $CO_2$ electrode 20 are bound by their respective membranes.

The membrane for the oxygen sensor may be fabricated from a polymeric material such as polystyrene in an organic or inorganic solvent. The oxygen permeable electrolyte of the oxygen sensor 24 bathes the anode 26 and cathode 34 to provide electrical ionic contact between the two. The electrolyte can be any electrolyte known to those skilled in the art for Clark Cell as, for example, a saline solution based on potassium chloride or sodium chloride.

The anode 26 of the oxygen sensor 24 is electrically grounded at 27 to assure that the electrolyte potential does not change and that the opening to the electrolyte is held at some voltage which is the same as the anode potential so that the electrolyte is grounded in the electrode configuration.

The reference electrode 30, which is located at the end of extension 32 and which extends from anode 26 of the oxygen sensor 24, provides a highly stable reference potential. This reference potential provided by the reference electrode 30 facilitates accurate measurement of the blood gases. The reference electrode 30 may be fabricated from a number of suitable materials known to those skilled in the reference electrode art such as a silver and silver chloride composite using the aforementioned layered circuit technique.

The thermistor 38 is a thick film thermally sensitive resistor whose conductivity varies with the changes in temperature. The thermistor 38 may be fabricated from a number semi-conductive materials as, for example, oxides of metals. The thermistor and may be formed and applied to the substrate layer 12 by the use of the aforementioned layered technique. The temperature coefficient of the thermistor 38 is large and negative and is used to sense the temperature of the board 10 at all times when the board 10 is coupled to its associated electronic analyzing module as shown in FIGS. 5 and 6. It is operated at relatively low current levels so the resistance is affected only by the ambient temperature and not by the applied current.

As before described, external leads 52 and 56 are in metallic electrical conducting contact with a thick film resistor 76 which is provided on the FIG. 2 side of the substrate layer 12. The resistor 76 is in an half-bridge relationship with the thermistor 38 and, as such, it commonly shares external lead 52 with the thermistor 38; thermistor 38 also being in metallic electrical conducting contact with external lead 52. The half-bridge circuit configuration is a voltage divider and generates a ratiometric output to the module. This is important for it allows the actual resistance values to float and results in highly consistent and accurate temperature sensing and control of the board 10 on a board to board basis. Accuracy and consistency of the resistor 76 and thermistor 38 arrangement is achieved by calibrating the board 10 by laser trimming of the resistor 76 to produce zero volts at 37° C. The laser beam is precisely deflected across the thick film resistor 76 to produce the desired temperature voltage relationship. A current is applied at external leads 50 and 52 by the module until zero volts is achieved. This gives a linear output so that the temperatures can be measured other than 37° C. from the slope of the line from the calibration at room temperature and 37° C. The resistor 76 has essentially zero temperature coefficient and, accordingly, may be placed without any adverse effect on the sensing capability of the associated thermistor 38, on the FIG. 2 side of the board 10 with the heater 74.

Accurate sensing of the ambient temperature of the board 10 is required to precisely control the heater 74 to ultimately maintain, within a narrow distribution of temperatures, the desired operating surface temperature on the FIG. 1 or sensor side of the board 10.

Placement of the thermistor 38 is another important aspect of the present invention. As can be seen in FIG. 1, the thermistor 38 is placed in the same plane and in close relation to the sensors 16, 20 and 24 to thereby accurately sense the ambient temperature at or near such sensors.

This physical placement of the thermistor 38 allows for the rapid adjustment of the heater 74 by the module to maintain the desired operating temperature. The thermistor 38 resistor 76 arrangement provides temperature measurement accuracy of within ±25° C.

This physical placement of the thermistor 38, so close to the sensors, requires that it be correctly fabricated to ensure that it is electrically isolated from the electrolytes of the several sensors. The encapsulant for the thermistor must be thick enough to accomplish the electrical isolation yet thin enough so as not to lose any response time.

The heater 74, provided on the FIG. 2 side of the board 10, rapidly and accurately produces the necessary heat in response to any temperature change sensed by the thermistor 38; the thermistor 38 and the several sensors 16, 20, and 24 all being in the heated region produced by the heater 74.

Thick film heaters are not generally considered to be rapid response devices and their heat output tends to take a relatively long time, in terms of electronic devices, to change. To improve the responsiveness of the heater 74, it is powered by a controlled DC voltage whereby the heater is regulated by a combination of proportional (P), integral (I) and/or derivative (D) controls, preferably PID control thereby reducing the amount of overshooting or undershooting by the heater of a predetermined temperature. This not only increases the responsiveness of the heater 74 but also allows for better overall thermal control including avoiding the heater 74 from overshooting or undershooting the desired temperature.

The timing sequence for the production of the heat by the heater 74 to the several sensors is provided by the natural state of power supplied to the board 10 when it is connected to the electronic module. This same power will also produce the read-out from the measurements by the sensors of the blood gas oxygen, carbon dioxide and pH. This timing sequence facilitates a room temperature calibration of the board 10; a elevated temperature calibration at 37° C. and then the measurement of the blood gas oxygen, carbon dioxide and pH.

Prior to any measuring of the blood gases by the several sensors 16, 20 and 24, all or part of the board 10 may be exposed to or stored with a calibration liquid, with the several sensors being exposed to the fluid. To measure the blood gases, the several sensors are brought in contact with the volume of the blood sample to be measured. The volume of the blood sample may be quite small, ranging from as small as a few microliters.

Figure 3:
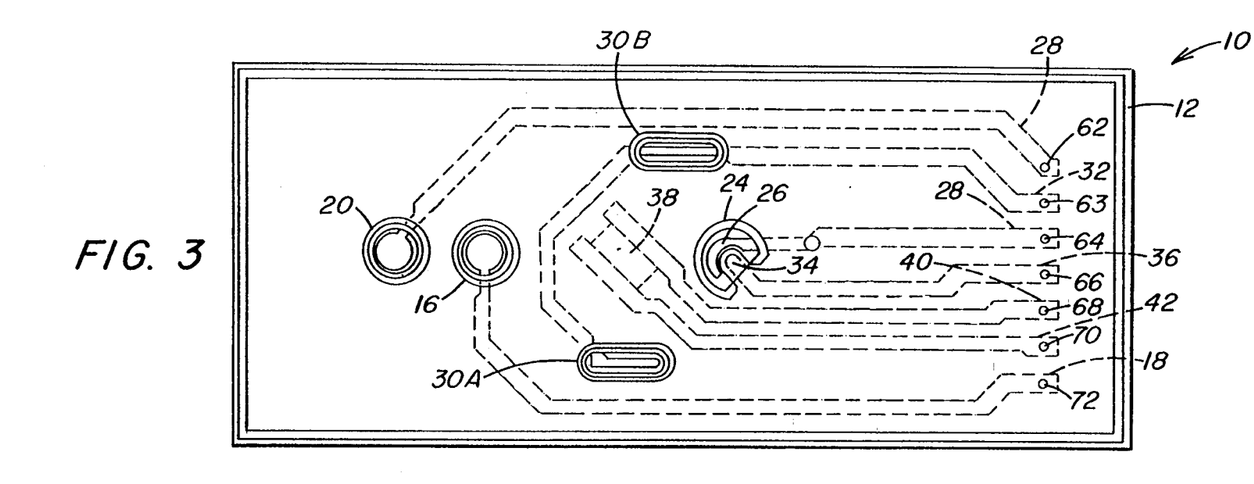
FIG. 3 is a planar view of the one side of the wiring substrate of the present invention, having an arrangement of three analyte sensors with two reference electrodes and a thermistor with accompanying patterned and layered circuitry.

FIG. 3 shows the preferred embodiment of the substrate of the present invention where two reference electrodes 30A and 30B are present in offline alignment to the alignment of the sensors 20, 16 and 24 and thermistor 38. The axial alignment shown in FIG. 3 allows the sensors to be in contact with a sample in a chamber covering their alignment, while the reference electrodes can be in contact with reference fluid or electrolyte in another chamber placed in fluid contact with the reference electrodes. Any alignment pattern can be used that separates the reference electrode from the sensors in the aforedescribed manner. The other components of the wiring board are as described for the other figures.

Figure 4:
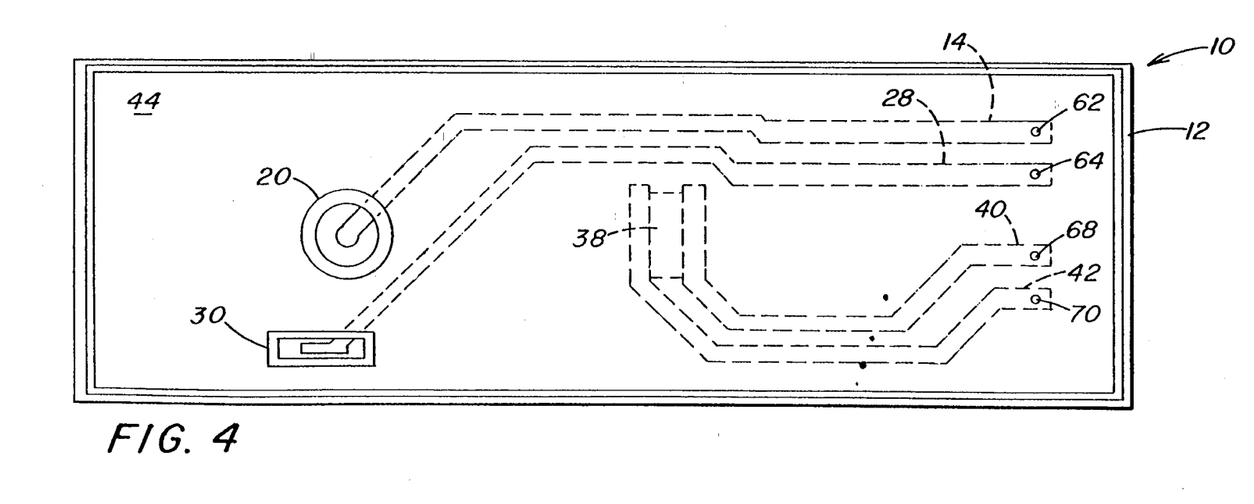
FIG. 4 is a planar view of the one side of the wiring substrate of a broad aspect of the present invention having one sensor and a thermistor axially aligned and one reference electrode spaced apart from that axis and having accompanying patterned and layered circuitry.

FIG. 4 shows a broader aspect of the invention where only one sensor 20 is present with one reference electrode 30. If the sensor does not require a reference electrode as in the case of most amperometric electrodes the reference electrode need not be present.

FIG. 5 shows the block diagram of the functions and interrelationship of these functions for the electronic analyzing module of FIG. 5, hereinafter referred to as Analyzer with its electrical connection to the patterned metallic layer 14 of FIGS. 1-4. The analog input processing unit 180 of the Analyzer interfaces with the electric circuitry patterned metallic layer 14 of the previous figures by the external leads 46-60 to allow signals from the sensing electrode 16, 20, and 24 and any temperature detector, thermistor; 38 of FIGS. 1, 3-4. Also the external leads 46-60 allows for electrical current to be supplied to any heater 74 and resistor 76 on board 10 as shown in FIG. 2 and for any current or voltage that may be needed by the sensors 18 on the board 10. The electrical connections to the external leads can be separate but are preferably individual connections in a bundle connector or ribbon cable. Connection 181 can carry current to an amperometric oxygen sensor 24 of FIG. 1. Respectively, connections 182, 183, 184, and 185 can carry signal and/or supply current or voltage to: the sensors 16 and 20, the thermistor 38, and heater 74 all shown in the previous FIG. 1 and 20. The processing unit 180 can be electrically connected to the microcomputer 187 by 186 to the function of a 12 bit analog to digital converter 188. Converter 188 can be electrically connected by 189 to line 200 a type of buss line. Through line 200 connections are made to the central processing unit (CPU) 201 which has is a date/-time circuit and battery backup random access memory device and can be and preferably is an 8-bit central processing unit (CPU) microprocessor. In addition the encoded information reader and drive circuit unit 190 is connected by line 191 to the microcomputer 187 through Input/Output (I/O) port 192 for two way communication. The CPU is connected through I/O port 195 to the display and keyboard unit 196, and this unit is connected through I/O port 197 and through line 202 to line 200 for communication with the microcomputer 187. The CPU 201 is connected for external communication by RS232 and drive circuit unit 203 through serial port 204. The microcomputer 187 is connected to a power supply 205 and battery pack 206 for power. Also input output port 208 is connected electrically to a printer mechanism 210 for a hard copy display.

In the preferred embodiment, the printed wiring board whose functions are depicted in FIG. 5 is divided into two boards subassemblies. First a primary board subassembly which is divided into five subsystems: the microcomputer, the bar code reader system, the printer subsystem, the sensor input circuits, and the RS232 drive circuit. The second subassembly is the power supply board subassembly which is a switch power supply with four outputs. One pair provides ±5 volts for the digital and the analog circuits. The other pair provides an isolated ±5 volts for the RS232 drive circuits. The microcomputer consists of four major subsections—the central processing unit, the program memory, the random axis memory, and address decoder and the analog digital converter. The CPU is preferably an 80 C51FA8 bit CMOS microcontroller with a 256×8 internal random axis memory and four 8 bit bi-directional parallel ports and three 16-bit timer/event counters and with full duplex programmable serial interface and reduced power modes. The CPU can address 64,000 bits of programmed memory and 64,000 bits of random access memory or memory map input/output. The program memory is preferably a 27C256 which is a high-density CMOS electrically programmable read only memory organized as a 32,768×8 configuration. The random access memory is divided into two types. First an 8,000×8 volatile static random access memory and a 2,000×8 nonvolatile RAM with a built-in real time clock that uses an embedded lithium energy cell to maintain the watch information and retain the RAM data for over five years. The address decoder is a GAL that selects seven memory mapped areas of random access memory and two are selected as data memory and the rest are selected as inputs or outputs. The analog digital converter is an ML2208 data acquisition peripheral that has an eight channel single ended multiplexer, a programmable game instrumentation amplifier, a 2.5 volt band gap reference, and a 12-bit+analog to digital converter with built-in sample-and-hold. The 8D converter interfaces to the microcontroller through the general purpose 8-bit port. Also, the ML2208 includes a programmable processor, data buffering, a 16-bit timer and limit alarms. The bar code read system consists of a 70 nanometer precision optical reflective sensor and the system uses the HPHBCS-1100 sensor and HP sapphire lens. A printer subassembly is a thermal printer subassembly having four main components—the 8-bit latch, a printer head drive, a motor drive circuit and the printer mechanism. The sensor input circuits are analog signal conditioning circuits that receive the signals from the sensors and electronically control the sensors. There are two types of signals from the sensors, voltage or current. In addition, there is the heater control circuit. The serial or port driver circuit consists of the RS232 input buffer and line driver that are optically isolated from the internal circuits of the analyzer. Isolation is necessary in order to comply with the UL544 leakage current requirement. The power supply circuit supplies the five volts to the logic circuits and the analog circuit and an isolated five volts for the serial port. Power to the printer motor and printer heads is supplied directed from the battery pack which is typically six volts.

Any components known to those skilled in the art to accomplish the aforementioned functions can be used in the analyzer and the electrical circuitry of the present invention.

Although a particular preferred arrangement for the functional units of the Analyzer has been specifically set forth variations are possible that may delete one or more of the functional units. As long as the processing unit 180, and converter unit 188 are present when analog signals are used, and a processor is functionally tied into these units and power is supplied and a read out can be obtained the Analyzer is usable for use with the board 10 in a housing. Appropriate software resides in the CPU to accomplish these connections and to convert signals from the sensors and to perform the calibration and analysis of samples and to give values indicating the specific amounts of the known types of analytes present in the analyzed fluids.

FIG. 6 depicts a flow chart for the software of the Analyzer. The software assists the analyzer in performing several function. One of these is in capturing dc voltage levels emitted from the analyte sensors preferably the oxygen, carbon dioxide, and the pH sensors that are on the board 10 in a housing. Another is in analyzing a sample by performing relative measurements on the sensor inputs, while still another is to provide an analysis report. In FIG. 6 the unit is turned on at 120, where the connector 122 indicates that the software during the initialization function is responsible for verifying the status of the electronic components on the board 10 and of the RS232 communication port, bar code, detection of the sensor element, non-volatile RAM checksum, ROM checksum, RAM check as indicated at 124 and the real-time clock, and valid date and time and display units and printer as indicated at 126. The diagnostic function is responsible for performing the requested diagnostic function. Diagnostic commands are received at the RS232 port. The diagnostic commands can be in the form of ASCII data in both upper and lower case alpha characters and the digits 0 thru 9. At the decision block 127, if the analyzer is connected to the sensor the software enters the calibration mode and the analysis mode and outputs results. In this operation the emitted sensor voltages are converted from analog data to 16 bit digital data and the signal levels are captured, averaged and stored for the calibrant. Signal values from these three sensors depict the entry and exit of calibration solution, sample to be analyzed within the sensor channel. Also the levels of the analytes that exist during the presence of each of the liquids being analyzed are depicted. The Units are measured for these variables of the analytes and displayed in millimeters of mercury when blood gases are the analytes. In the signal processing phase of the software events are encompassed such as the detection of introduction of the calibrant solution, setting of any temperature of the calibration solution, introduction of the sample, and analysis of the sample. References to signal data are interpreted as relative and not absolute. Detecting the entrance, exit and temperature of a sample liquid like blood is performed by comparing present sensor values processed by the analog to digital converter to previous sensor values. Rise, fall and stabilization of a sensors signal is the means used in detecting a change occurred in the sensor component. The outputs of the analyzer are analog voltages corresponding to relative levels of the analytes in the sample fluid at the sensor temperature. These voltages are sampled and converted to a digital value many times per second. Once each second these values are averaged to provide a smoothed estimate of the parameter value. The quantitization is bipolar with an good accuracy. Changes in the signal levels are used to detect introduction of the calibrant and to validate sensor operation. The values measured at the set temperature for the calibrant and sample are used to calculate the test results. The input units can be millivolts and nanoamperes. Once the analyte levels are obtained from the sample like blood gas the analysis is performed. This is done by the execution of a series of known mathematical equations using the analyte data as input. Intercept and slope is entered in the system via the bar code reader. After the analysis and display of the results electronically and/or by hard copy the software enters the connector and allows for the analyzer to power down and turn off.

We claim:

1. An improved electronic wiring board having a nonconducting substrate, temperature sensor and at least one analyte sensor supported, in close relation, one to the other, on the same side of said substrate and a heater, also supported on the substrate, and located on another side of said substrate from the temperature sensor and analyte sensor to provide heat in response to temperature sensed by said temperature sensor to at least the region where said temperature sensor and said analyte sensor are positioned on said substrate to thereby control the temperature of said region of said board within a narrow distribution of temperatures, and connecting means supported on said substrate for connecting said board to an external electrical source.

2. The improved electronic wiring board of claim 1, wherein said board is manufactured using thick film layered circuit technique.

3. The improved electronic wiring board of claim 1, wherein said temperature sensor is a thermistor and said analyte sensor is at least one blood gas sensor, where the temperature sensor and the analyte sensor are supported in the same plane on said board.

4. The improved electronic wiring board of claim 3, wherein said blood gas sensor is at least an oxygen sensor.

5. The improved electronic wiring board of claim 3, wherein said blood gas sensor is at least a carbon dioxide sensor.

6. The improved electronic wiring board of claim 3, wherein said blood gas sensor is at least a pH sensor.

7. The improved electronic wiring board of claim 3, wherein said blood gas sensor includes an oxygen sensor, a carbon dioxide sensor and a pH sensor.

8. The improved electronic wiring board of claim 3, wherein the substrate of said board is a flat substantially thin ceramic substrate layer.

9. The improved electronic wiring board of claim 8, wherein said board includes a patterned metallic layer provided on said ceramic substrate layer.

10. The improved electronic wiring board of claim 9, wherein said metallic layer is formed on said substrate by depositing a metallic printing paste on said substrate to form electronic conducting pathways and the electrodes of said sensors and the electrode of a reference electrode.

11. The improved electronic wiring board of claim 10, wherein said metallic layer is encapsulated with at least one layer of a chemically stable and moisture resistant encapsulant.

12. The improved electronic wiring board of claim 8, wherein the thermistor is on the ceramic substrate layer, and said thermistor is encapsulated with at least one substantially thin layer of a chemically stable and moisture resistant encapsulant.

13. The improved electronic wiring board of claim 1, which includes a control means electrically connected to the board for receiving the output from the temperature sensor and to power the heater to control the temperature of said region of said substrate within a narrow distribution of temperatures to adjust the temperature for maintenance of the operating temperature.

14. The improved electronic wiring board of claim 1, which includes a means for containing fluid on the board in contact with the at least one analyte sensor.

15. The improved electronic wiring board of claim 1, wherein said heater is powered by pulsed DC whereby said heater is continually turned on and off thereby avoiding said heater from overshooting or undershooting a predetermined temperature.

16. The improved electronic wiring board of claim 1, wherein said the temperature sensor senses the ambient temperature of the board and the heater heats the board within the temperature range of ambient to 37° C.±25° C.

17. An improved electronic wiring board having a nonconducting substrate, temperature sensor and at least one analyte sensor supported, in close relation, one to the other, on the substrate and a heater, also supported on the substrate, to provide heat in response to temperature sensed by said temperature sensor to provide heat to at least the region where said temperature sensor and said analyte sensor are positioned on said board to thereby control the temperature of said region of said board within a narrow distribution of temperatures, connecting means supported on said substrate for connecting said board to an external electrical source where the connecting means has a plurality of external leads, a resistor which is supported on said board on the same side as said heater and commonly connected to one of said external leads with said thermistor, dividing the voltage therebetween.

18. The improved electronic wiring board of claim 17, wherein the temperature coefficient of said thermistor is negative or positive and the temperature coefficient of said resistor is substantially zero, and where the divided voltage is proportional or inversely proportional to temperature, the this output is used to measure temperature.

19. The improved electronic wiring board of claim 18, wherein said connecting means further includes a plurality electronic conducting pathways individually and electrically connecting each of said sensors and said thermistor with external leads provided on said board at the end of said pathways.

20. The improved electronic wiring board of claim 19, wherein said resistor and said heater are each electrically connected to external leads.

21. The improved electronic wiring board of claim 20, wherein said heater is powered by pulsed DC whereby said heater is continually turned on and off thereby avoiding said heater from overshooting or undershooting a predetermined temperature.

22. The improved electronic wiring board of claim 19, wherein said external leads are positioned on the same side of said board as said resistor and said heater.

23. The improved electronic wiring board of claim 22, wherein said electronic conducting pathways individually and electrically connecting each of said sensors and said thermistor on one side of said board with external leads provided on the other side of said board through a plurality of holes in said board.

24. The improved electronic wiring board of claim 19, wherein said thermistor and resistor are calibrated by laser trimming of said resistor.

25. The improved electronic wiring board of claim 24, wherein said oxygen sensor is an electrochemical cell and includes a anode and a cathode, each connected to an external lead.

26. The improved electronic wiring board of claim 25, wherein said oxygen sensor has an oxygen permeable membrane covering, in a fluid tight manner, a means with an opening in said board to contain an electrolyte, said anode being grounded on said board to thereby assure that potential of said electrolyte is the same as the anode potential.

27. The improved electronic wiring board of claim 26, which includes at least one reference electrode, to provide an accurate reference potential, supported on said board and is electrically connected to a electronic conducting pathway.

28. The improved electronic wiring board of claim 27, wherein there is one reference electrode supported on said board that is electrically connected to a electronic conducting pathway extending from said anode.

29. The improved electronic wiring board of claim 23, wherein the heater occupies the opposite side of the board from the thermistor and sensor and has a serpentine circuit layout.

30. The improved electronic wiring board of claim 23, wherein at least one analyte sensor is a thick film electrode sensor with at least one polymeric membrane and electrolyte.

31. An improved temperature control apparatus for an analyte sensor, comprising:
a) electronic wiring board having a nonconducting substrate, temperature sensor and at least one analyte sensor supported, in close relation, one to the other, on the substrate and a heater, also supported on the substrate, and located on the substrate to provide heat in response to temperature sensed by said temperature sensor to at least the region where said temperature sensor and said analyte sensor are positioned on said substrate;
b) connecting means supported on said substrate for connecting said board to an external control means; and
c) control means to receive the output from the temperature sensor and power the heater to control the temperature of said region of said substrate within a narrow distribution of temperatures.

* * * * *